United States Patent [19]

Hazony

[11] Patent Number: 5,492,014
[45] Date of Patent: Feb. 20, 1996

[54] ULTRASONIC TRANSDUCER FOR MONITORING ACOUSTIC EMISSIONS

[75] Inventor: Dov Hazony, University Heights, Ohio

[73] Assignee: J. W. Harley Inc., Twinsburg, Ohio

[21] Appl. No.: 176,536

[22] Filed: Jan. 3, 1994

[51] Int. Cl.$^6$ .................................................. G01N 29/28
[52] U.S. Cl. .................................................. 73/644; 73/629
[58] Field of Search ..................... 73/632, 642, 661, 73/644, 597; 128/662.03, 660.1

[56] References Cited

U.S. PATENT DOCUMENTS

| | | | |
|---|---|---|---|
| 3,512,402 | 5/1970 | Foster | 73/661 |
| 4,398,424 | 8/1983 | Abts | 73/632 |
| 4,455,873 | 6/1984 | Abts | 73/632 |
| 4,658,650 | 4/1987 | Yorinaga | 73/632 |
| 4,907,454 | 3/1990 | Hazony | 73/597 |
| 4,918,990 | 4/1990 | Fowler | 73/632 |

*Primary Examiner*—Sandra L. O'Shea
*Assistant Examiner*—Christine K. Oda
*Attorney, Agent, or Firm*—James A. Hudak

[57] ABSTRACT

An ultrasonic piezoelectric transducer for monitoring acoustic events in a medium is disclosed. The transducer includes an elongated body member having a blind bore therein, a piezoelectric crystal which is received in the blind bore within the body member and which contacts the bottom surface thereof, and a rod which is received in the blind bore and which firmly contacts the piezoelectric crystal compressing the crystal against the bottom of the blind bore. The tip of the elongated body member has a convex configuration forming a lens permitting the interception of acoustic events over a wide angle and the direction of same toward the piezoelectric crystal for monitoring and detection purposes.

8 Claims, 2 Drawing Sheets

ULTRASONIC TRANSDUCER FOR MONITORING ACOUSTIC EMISSIONS

TECHNICAL FIELD

The present invention relates, in general, to electrical monitoring devices and, more particularly, to devices for monitoring acoustic events within liquid and/or gas filled apparatus.

BACKGROUND ART

The monitoring of high voltage, oil-filled electrical apparatus, such as transformers, reactors and capacitors, for the occurrence of acoustic events therein, is very desirable from a quality assurance standpoint. Such events could result from partial electrical discharges, magnetic domain switching (Barkhausen effect), high frequency mechanical vibrations, transformer tap changing, rainstorm or thunderstorm effects, and the like. With respect to partial electrical discharges, such discharges can degrade the insulation within the high voltage electrical apparatus causing the eventual breakdown of same. Thus, it is desirable to provide a device for detecting partial electrical discharges before such discharges increase to a level which may cause extensive damage to the insulation within the high voltage apparatus.

Various devices and methods are available for monitoring the occurrence of partial electrical discharges within oil-filled electrical transformers and high voltage capacitors. For example, a typical prior art method for detecting and locating partial electrical discharges within a transformer uses the electrical signal produced by the discharge. Another approach utilizes a signal responsive to the pressure pulse induced in the oil from the discharge to determine the intensity and approximate location of the partial electrical discharge within the transformer.

Rather than utilizing the electrical signal produced by or resulting from the partial electrical discharge, other detection devices monitor the acoustic events resulting from the partial electrical discharge. Such devices might use fiberglass rods which are located within the oil-filled transformer and which act as wave guides for transmitting the acoustic emissions resulting from the partial electrical discharges to sensors located exteriorly of the transformer. It has been found that such rods or wave guides have a tendency to impart their own acoustic properties on the signal being monitored thus degrading the performance of the detection device. Still another approach involves exteriorly affixing an acoustic sensor to the outer walls of the transformer. An inherent problem associated with this approach is that the resonances of the outer wall of the transformer degrade the performance of the device in a frequency range that is significant. In addition, spurious signals, such as those produced during a rainstorm or a thunderstorm, can degrade the acoustic signals detected by the device.

In view of the foregoing, it has become desirable to develop a device for detecting an acoustic event which is simple in construction and operation, rugged and durable so as to be capable of withstanding the aggressive environment that exists within an oil-filled apparatus, and which can accurately detect acoustic events from within the apparatus over an extended period of time.

SUMMARY OF THE INVENTION

The present invention provides an improvement over the prior art devices and methods for detecting partial electrical discharges within an oil-filled apparatus by providing a novel monitoring probe which can be inserted through the wall of the apparatus so as to be immersed in the oil within same. The probe includes an elongated body portion which is immersed in the oil within the apparatus, a piezoelectric crystal which is received in a blind bore within the elongated body portion and which contacts the bottom of the blind bore, and a rod which is received in the blind bore and which firmly contacts the piezoelectric crystal compressing same against the bottom of the blind bore. The tip of the elongated body portion has a convex configuration which forms a lens permitting the interception of acoustic fields and emissions over a very wide angle and which directs same toward the piezoelectric crystal for monitoring and detection. Interception of an acoustic field or emission by the piezoelectric crystal causes the crystal to produce an electrical signal which is transmitted to detecting apparatus via the connecting rod. The material comprising the outer jacket of the probe and the connecting rod have similar thermal expansion coefficients so as to maintain firm electrical and acoustical contact over a wide operating temperature range.

In addition to being able to accurately detect acoustic events in an oil-filled apparatus, the present invention can also determine the temperature of the oil within same. Such temperature detection can be obtained by utilizing the piezoelectric crystal to transmit an interrogating pulse through the blind base into the lens and to detect the return pulse frown the oil side of the tip of the elongated body portion of the monitoring probe.

DESCRIPTION OF THE PREFERRED EMBODIMENT

Figure 1:
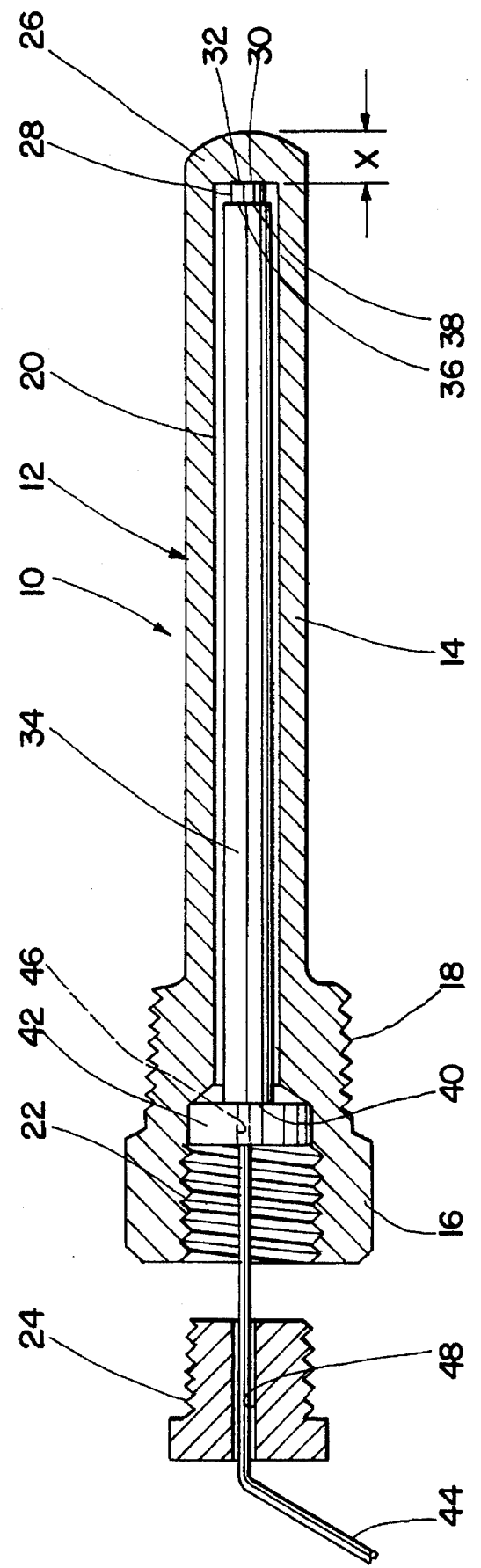
FIG. 1 is a cross-sectional view of the monitoring probe of the present invention.

Referring now to the drawings where the illustrations are for the purpose of describing the preferred embodiment of the present invention and are not intended to limit the invention described herein, FIG. 1 is a cross-sectional view of a probe 10 which can be utilized to monitor and detect acoustic events, such as those resulting from partial electrical discharges within an oil-filled apparatus. The probe 10 includes outer jacket 12 comprising an elongated body portion 14, an end portion 16 having a square, hexagonal or octagonal configuration permitting the gripping of same, and a threaded portion 18 interposed between the elongated body portion 14 and the end portion 16. A blind bore 20 is provided within the elongated body portion 14 and within a portion of the threaded portion 18. A counter bore 22 is provided within the end portion 16 and terminates in the blind bore 20. A portion of counter bore 22 is threaded to receive a mating threaded cap 24. It should be noted that the foregoing outer jacket 12 may be similar to that utilized in so called "thermal wells" which are typically inserted into oil-filled transformers to measure the temperature of the oil therein.

The blind bore 20 and the counter bore 22 are concentric with a longitudinal axis of the probe 10. The tip 26 of the elongated body portion 14 has a convex configuration forming a lens (fish-eye) whose function will be described later herein. A piezoelectric crystal 28 is received within blind bore 20 and a surface 30 of the crystal 28 contacts the bottom 32 of blind bore 20. A rod 34 having a diameter slightly less than the diameter of the blind bore 20 is received within bore 20 and its end 36 contacts surface 38 of the piezoelectric crystal 28. The opposite end 40 of rod 34 contacts an insulating washer 42 which is received within counter bore 22 and interposed between rod 34 and threaded cap 24 after cap 24 is threadably received within counter bore 22. Tightening of the cap 24 within the outer jacket 12 causes the rod 34 to apply a compressive force to the piezoelectric crystal 28 resulting in a firm electrical contact between end 36 of rod 34 and surface 38 of crystal 28 and between surface 30 of crystal 28 and bottom 32 of blind bore 20. An electrical conductor 44 is connected to end 40 of rod 34 and is received through apertures 46 and 48 in washer 42 and cap 24, respectively, for a connection to a detection device (not shown). Rod 34 and/or elongated body portion 14 can be threaded for all or a portion of their respective lengths to improve the acoustic performance of the probe 10 by suppressing undesired signals, as hereinafter described. Regardless of whether the rod 34 is threaded for all or a portion of its length, strips of tape can be applied to the surface thereof in a spaced-apart relationship to electrically insulate the rod 34 from the outer jacket 12. The end 40 of rod 34 is electrically insulated from the jacket 12 by insulating washer 42.

Figure 2:
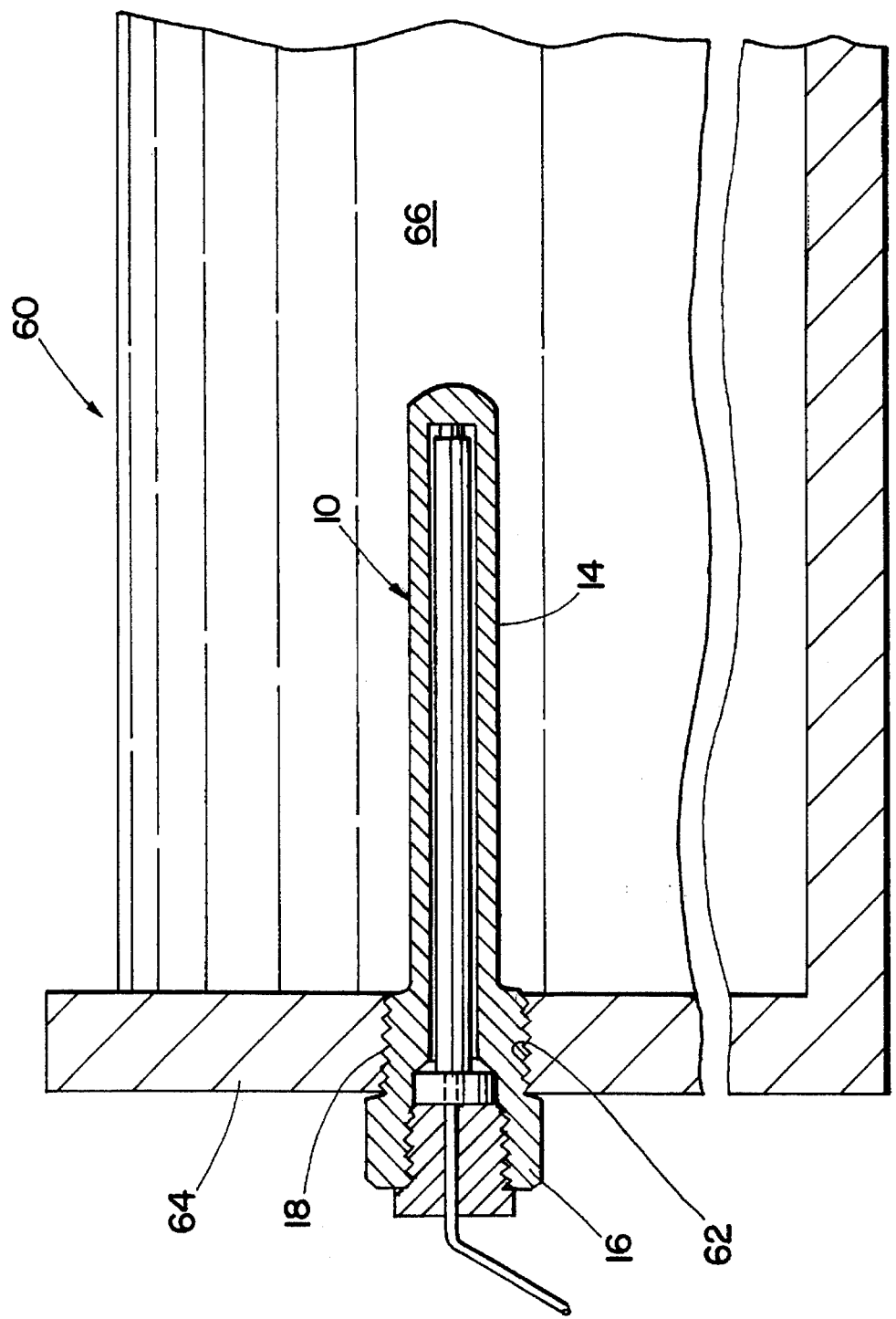
FIG. 2 is a cross-sectional view of the monitoring probe of the present invention installed within an oil-filled transformer.

Referring now to FIG. 2, the installation of the probe 10 within an oil-filled transformer 60 is illustrated. The probe 10 is inserted through an aperture 62 within a wall 64 of transformer 60 and is threadably retained therein by threaded portion 18 which engages mating threads provided within aperture 62. The position of the aperture 62 within wall 64 is such that elongated body portion 14 of probe 10 is immersed in the oil 66 within the transformer 60, and end portion 16 of probe 10 is positioned adjacent to and exteriorly of the wall 64 of the transformer 60.

Operationally, when an acoustic event is created within the transformer 60 as a result of a partial electrical discharge or other disturbance therein, the acoustic field or emission resulting therefrom is intercepted by the tip 26 of the elongated body portion 14 of the probe 10. The convex configuration of the tip 26 of the elongated body portion 14 acts as a "wide-angle" lens to intercept the acoustic field or emission over a wide angular area and direct same toward the piezoelectric crystal 28. The thickness of the tip 26 of elongated body portion 14, shown as distance "x" in FIG. 1, is minimized in order to reduce losses and to insure that the acoustic resonance frequency of tip 26 is significantly greater than the frequency band of interest, which is quite broad. The piezoelectric crystal 28 converts the acoustic field or emission into electrical pulses which are transmitted via rod 34 to the electrical conductor 44 which passes through the apertures 46 and 48 in washer 42 and cap 24, respectively. The geometry of the elongated body portion 14 is such that its length is substantially greater than its diameter so as to minimize the effects of possible mechanical resonances on the designated frequency response of the probe 10. Similarly, the threads on the outer surface of the elongated body portion 14 and/or the rod 34 minimize the effects of spurious mechanical vibrations and stray signals arriving at the piezoelectric crystal 28 by paths other than through the tip 26 of the elongated body portion 14 of the probe 10..

The proper selection of the material for the outer jacket 12 and the rod 34 is important since both of these members should have similar thermal expansion coefficients so that firm electrical and acoustical contact is maintained between the end 36 of rod 34 and jacket 12, via piezoelectric crystal 28, over a wide operating temperature range. In order to ensure the maintenance of good electrical and acoustical contact within the probe 10, the outer jacket 12 and the rod 34 should be fabricated from the same, or similar, material.

In addition to monitoring acoustic events, the probe 10 can be utilized to monitor and/or determine the temperature of the oil 66 within the transformer 60. Since the distance "x" from the bottom 32 of the blind bore 20 to the surface of the tip 26 on elongated body portion 14 is known, an interrogating pulse can be supplied to the piezoelectric crystal 28 via the electrical conductor 44 and the rod 34. A return pulse from the oil side of the tip 26 of body portion 14 re-excites the piezoelectric crystal 28 causing an electrical pulse to be transmitted through the rod 34 and the electrical conductor 44 to a detection device (not shown). Since the distance "x" is known, by measuring the time interval between the transmission of the interrogating pulse and the receipt of the return pulse, the temperature of the tip 26 of body portion 14, and thus the temperature of the oil 66 within the transformer 60, can be determined.

In summary, the present invention not only permits remote sensing of acoustic events within an oil-filled apparatus but also allows determination of the temperature of the oil within same. The tip 26 on the elongated body portion 14 forms a lens ("fish-eye") permitting the interception of acoustic events over a very wide angle and over a wide frequency range. Threading on the outer surfaces of the elongated body portion 14 and/or the rod 34 minimizes the responsiveness of the probe to extraneous noise within the oil-filled apparatus. Lastly, by proper selection of the material comprising the outer jacket 12 and the rod 34, the overall signal to noise ratio of the probe 10 can be enhanced.

Certain modifications and improvements will occur to those skilled in the art upon reading the foregoing. It should be understood that all such modifications and improvements have been deleted herein for the sake of conciseness and readability, but are properly within the scope of the following claims.

I claim:

1. A piezoelectric ultrasonic transducer device for monitoring acoustic events occurring within a medium subjected to electric and magnetic fields comprising an elongated body member having a blind bore therein and terminating in a substantially continuous convex surface, at least a portion of said elongated body member and said substantially continuous convex surface being receivable within the medium being monitored, a piezoelectric element received in said blind bore in said elongated body member and positioned therein so as to contact the surface defining the bottom of said blind bore and means for biasing said piezoelectric element causing said piezoelectric element to firmly contact said surface defining the bottom of said blind bore, said substantially continuous convex surface intercepting acoustic events occurring within the medium and directing said acoustic events towards said piezoelectric element for monitoring purposes.

2. The transducer device as defined in claim 1 wherein said substantially continuous convex surface is adjacent said surface defining the bottom of said blind bore in said elongated body member.

3. The transducer device as defined in claim 1 wherein said biasing means comprises a rod member having oppositely disposed first and second ends and means for applying a compressive force to said first end of said rod member, said rod member being receivable in said elongated body member and being positioned therein so that said second end of said rod member contacts said piezoelectric element.

4. The transducer device as defined in claim 3 further including spacer means interposed between said first end of said rod member and said force applying means.

5. The transducer device as defined in claim 4 wherein said spacer means is an insulating washer.

6. The transducer device as defined in claim 1 wherein at least a portion of said elongated body member is threaded.

7. The transducer device as defined in claim 3 wherein at least a portion of said rod member is threaded.

8. The transducer device as defined in claim 3 wherein the material comprising said elongated body member and said rod member have similar thermal expansion properties.

* * * * *